US006835849B2

(12) United States Patent
Manzer

(10) Patent No.: US 6,835,849 B2
(45) Date of Patent: Dec. 28, 2004

(54) SYNTHESIS OF ALKENOATE ESTERS FROM LACTONES AND ALCOHOLS

(75) Inventor: Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/618,128

(22) Filed: Jul. 11, 2003

(65) Prior Publication Data

US 2004/0059152 A1 Mar. 25, 2004

Related U.S. Application Data

(60) Provisional application No. 60/396,069, filed on Jul. 15, 2002.

(51) Int. Cl.[7] .......................... C07C 67/27; C07C 67/30

(52) U.S. Cl. .................. 560/205; 560/211; 560/214; 560/217

(58) Field of Search .......................... 560/205, 211, 560/214, 217

(56) References Cited

U.S. PATENT DOCUMENTS

| 3,031,493 A | 4/1962 | Enk et al. |
| 4,740,613 A | 4/1988 | Fischer et al. |
| 4,777,285 A | 10/1988 | Kummer et al. |
| 5,144,061 A | 9/1992 | Hoelderich et al. |

*Primary Examiner*—Ba K. Trinh
(74) *Attorney, Agent, or Firm*—Gerald E. Deitch

(57) ABSTRACT

The invention relates to the synthesis of alkenoate esters from a corresponding lactone and an alcohol in the presence of a basic catalyst. More specifically, this invention relates to the synthesis of methyl-4-pentenoate ester from 5-methyl butyrolactone and methanol.

15 Claims, No Drawings

SYNTHESIS OF ALKENOATE ESTERS FROM LACTONES AND ALCOHOLS

This application claims benefit of Ser. No. 60/396,069, filed Jul. 15, 2002.

FIELD OF INVENTION

This invention relates to the synthesis of alkenoate esters from a corresponding lactone and an alcohol, in the presence of basic catalyst. More specifically, this invention relates to the synthesis of alkyl-4-pentenoate esters from 5-methylbutyrolactone and alcohols.

TECHNICAL BACKGROUND

Alkenoate esters are valuable precursors and monomers in many processes, for example, in nylon intermediates such as caprolactam and adipic acid. For example, methyl-4-pentenoate ester is a precursor for the production of 5-formylvalerates, which can subsequently be converted to caprolactam without producing ammonium sulfate, by hydrogenation and cyclization of aminocaproates. U.S. Pat. No. 5,144,061 discloses a process for preparing alkenoate esters with a terminal double bond starting from a corresponding 5-, 6-, or 7-membered lactone and an alcohol, in presence of an acid catalyst.

U.S. Pat. No. 4,740,613 discloses preparation of 4-pentenoate esters by reaction of gamma-valerolactone with an alcohol in the presence of acidic catalyst at temperatures of 150° C. to 400° C. The reaction produces an isomeric mixture of 4-pentenoate, 3-pentenoates (cis structure and trans structure), and 2-cis-pentenoate. This reaction is represented by the following equation:

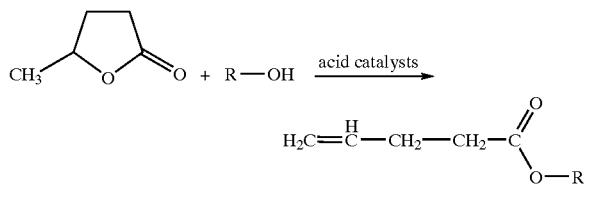

g-valerolactone alcohol mixture of isomeric pentenoates wherein, R is an alkyl group of 1 to 6 carbon atoms.

More specifically, the '613 patent disclosed the reaction of gamma-valerolactone and methanol in the presence of acidic catalysts to give a mixture of methyl pentenoate ester isomers: (1) methyl4-pentenoate ester, (2) cis-methyl-3-pentenoate ester, (3) trans-methyl-3-pentenoate ester and (4) cis-methyl-2-pentenoate ester. This reaction is represented as follows:

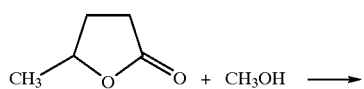

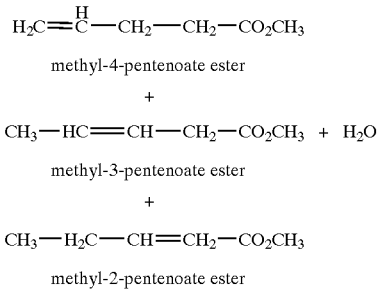

methyl-4-pentenoate ester
+
$CH_3-HC\!=\!CH-CH_2-CO_2CH_3 + H_2O$
methyl-3-pentenoate ester
+
$CH_3-H_2C-CH\!=\!CH_2-CO_2CH_3$
methyl-2-pentenoate ester Based on the final composition of all pentenoate esters in the product, the '613 patent discloses a maximum distribution of the methyl-4-pentenoate ester of 38%. Attempts prior to the '613 patent reported a maximum distribution of 8% of methyl-4-pentenoate ester (German Laid-Open Application DOS No. 3,412,295 as cited by the '613 patent). In these prior reactions, methyl-4-pentenoate ester was obtained by isomerization of methyl-3-pentenoate ester (70% trans, 30% cis). The 4-pentenoate product was subsequently isolated from such isomeric mixtures by azeotropic distillation.

However, employing the process conditions of the '613 patent cannot yield a methyl4-pentenoate ester distribution substantially higher than 38%. Thus, expensive steps for separation of methyl4-pentenoate ester (e.g. distillation) and recycling of the methyl-2- and the methyl-3-pentenoate esters isomers are necessitated. These prior disclosures demonstrate a continuing need for a process for directly producing methyl-4-pentenoate ester as opposed to converting methyl-3-pentenoate ester isomer to methyl-4-pentenoate ester. Consequently, a process which yields a higher selectivity and distribution of 4-pentenoates and a higher conversion of the lactones is desired.

Moreover, although each pentenoate ester isomer can be converted to another isomer, a simple process that produces a particular desired isomer as the major product would be advantageous.

The present invention teaches away from using the acidic catalyst for producing alkenoate esters from lactone and alcohol precursors. The invention teaches a process of using basic catalysts to produce alkenoate esters from lactone and alcohol precursors. Three main objectives are achieved from the process disclosed herein: (1) a higher selectivity of 4-pentenoates than hitherto known; (2) a desired distribution of methyl4-pentenoate; and (3) a higher conversion of the lactone precursor to product. Specifically, the process of the invention provides a selectivity of the methyl-4-pentenoates ester greater than 95%, a distribution of the methyl-4-pentenoate ester isomer in the methyl pentenoate ester product of up to 99% and a corresponding conversion of gamma-valerolactone as high as 70% employing the basic catalyst systems disclosed herein. Moreover, the process of the instant invention provides a direct, one step method of obtaining a higher yield of methyl-4-pentenoate ester.

SUMMARY OF THE INVENTION

This invention relates to a process for preparing at least one isomer of alkyl alkenoate ester (III) comprising the steps of contacting lactones of Formula I with an alkanol of Formula II in the presence of a heterogeneous base catalyst to form a mixture containing the corresponding alkyl alkenoate esters,

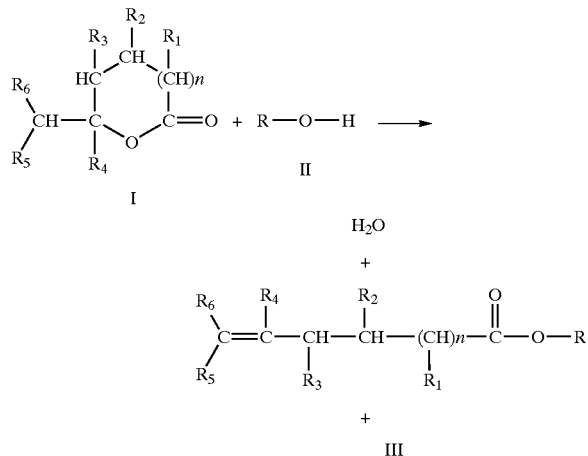

wherein: n=0–2; $R_1$, $R_2$, $R_3$, and R4 taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aryl, and unsubstituted or substituted heteroaryl, $R_5$ and $R_6$ taken independently are hydrogen or alkyl with 1 to 5 carbon atoms, wherein the total number of carbons of $R_5$ and $R_6$ do not exceed 5, and R is alkyl with 1 to 6 carbon atoms.

This invention specifically relates to a process for preparing alkyl-4-pentenoate ester isomer in high yields by contacting gamma-valerolactone with alcohol in presence of heterogeneous basic catalyst in the temperature range of from about 250° C. to about 500° C.

DETAILED DESCRIPTION OF THE INVENTION

The following abbreviations are used in the discussion that follows and are useful in understanding the meaning and scope of the invention.

"Alkyl" refers to an alkyl group up to and including 12 carbons. Common examples of alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl.

"Aryl" refers to a group defined as a monovalent radical formed by removal of a hydrogen atom from a hydrocarbon that is structurally composed entirely of one or more benzene rings. Common examples of aryl groups include benzene, biphenyl, terphenyl, naphthalene, phenyl naphthalene, and naphthylbenzene.

"Heteroaryl" refers to unsaturated rings of 5 or 6 atoms containing one or two O and S atoms and/or one to four N atoms provided that the total number of hetero atoms in the ring is 4 or less, or bicyclic rings wherein the five or six membered ring containing O, S, and N atoms as defined above is fused to a benzene or pyridyl ring. Common examples are furan and thiophene.

"Hydrocarbyl" refers to monovalent groups of atoms containing only carbon and hydrogen, and may be chiral or achiral. Unless otherwise stated, it is preferred in the method of the invention that hydrocarbyl (and substituted hydrocarbyl) groups contain 1 to 30 carbon atoms.

"Substituted" refers to a group attached to a reactant containing one or more substituent groups that do not cause the compound to be unstable or unsuitable for the use of reaction intended. Substituent groups useful in the method of the invention include nitrile, ether, ester, halo, amino (including primary, secondary and tertiary amino), hydroxy, oxo, vinylidene or substituted vinylidene, silyl or substituted silyl, nitro, nitroso, sulfinyl, sulfonyl, sulfonic acid alkali metal salt, boranyl or substituted boranyl, and thioether groups.

"Distribution" refers to the weight percent of a particular methyl pentenoate ester in total amount of methyl pentenoate product.

"Selectivity" refers to the weight percent of a particular methyl pentenoate in the total product weight including the weight of unreacted reactants).

"Conversion" refers to the weight percent of a particular reactant that is converted to product.

The present invention provides a process for the preparation of one or more pentenoate esters and isomers thereof of a general Formula III comprising contacting at least one lactone of Formula I with at least one alcohol of Formula II, in the presence of a heterogeneous base catalyst to form a reaction mixture containing the corresponding isomers of alkenoate esters, as represented by the following reaction equation,

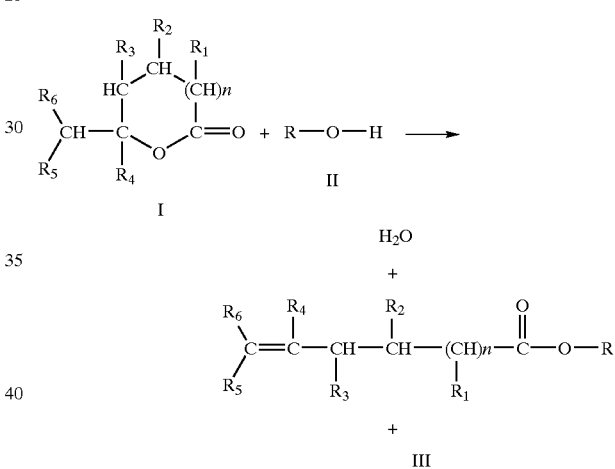

wherein: n=0–2; $R_1$, $R_2$, $R_3$, and $R_4$ taken independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aryl, and unsubstituted or substituted heteroaryl, $R_5$ and $R_6$ taken independently are hydrogen or alkyl with 1 to 5 carbon atoms, wherein the total number of carbons of $R_5$ and $R_6$ do not exceed 5. R is alkyl with 1 to 6 carbon atoms.

In a preferred embodiment, n=0. More preferably, n=0 and $R_1$, $R_2$, $R_3$, and $R_4$, taken independently, are hydrogen or alkyl. In a further preferred embodiment, n=0, and $R_1$, $R_2$, $R_3$, and $R_4$, taken independently, are hydrogen.

In another preferred embodiment, n=0, and $R_1$, $R_2$, $R_3$, $R_4$, $R_5$, and $R_6$ taken independently, are hydrogen. It is further preferred that where n=0, $R_1$, $R_2$, $R_3$, $R_4$, $R_5$, and $R_6$ independently are hydrogen in the lactone precursor, the R group of the alcohol precursor is a methyl group. The unsaturated pentenoate esters that are produced by the instant process can be one particular compound or a mixture of isomers. In this particular embodiment, the lactone is gamma-valerolactone (Formula IV) (also known as gammamethylbutyrolactone, gamma-pentalactone, and 4-methylbutyrolactone) and the alcohol is methanol (Formula V). One or more of the following unsaturated pentenoate esters (Formula VI) are produced therefrom: (1) cis-methyl-2-pentenoate ester, (2) trans-methyl-2-pentenoate ester, (3) cis-methyl-3-pentenoate ester, (4) trans-methyl-3-pentenoate ester, and (5) methyl-4-pentenoate ester.

This reaction is represented as follows:

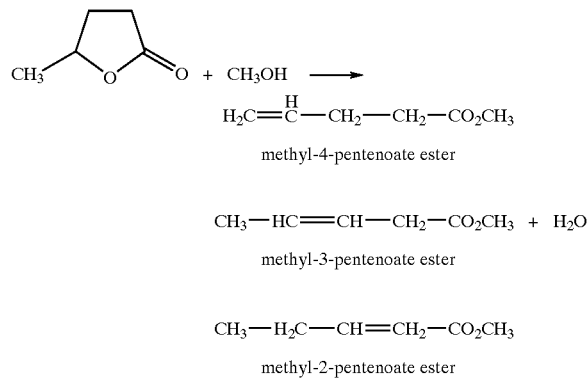

methyl-4-pentenoate ester $CH_3-HC=CH-CH_2-CO_2CH_3 + H_2O$ methyl-3-pentenoate ester $CH_3-H_2C-CH=CH_2-CO_2CH_3$ methyl-2-pentenoate ester The catalyst useful in the invention is a substance that affects the rate of the reaction but not the reaction equilibrium, and emerges from the process, chemically unchanged. A chemical promoter generally augments the activity of a catalyst. The promoter herein may be incorporated into the catalyst during any step in the chemical processing of the catalyst constituent. The chemical promoter generally enhances the physical or chemical function of the catalyst agent, but can also be added to retard undesirable side reactions.

"Heterogeneous catalyst" refers to a catalyst that operates on reactions taking place on surfaces where the reacting species are held on the surface of the catalyst by adsorption.

A suitable base catalyst useful in the process of the invention is either a substance which has the ability to accept protons as defined by Brönsted, or as a substance which has an unshared electron pair with which it can form a covalent bond with an atom, molecule or ion as defined by Lewis. A further description of base catalysts and how to determine whether a particular catalyst is basic is provided in Tanabe, K., *Catalysis: Science and Technology*, Vol. 2, pg 232–273, ed. Anderson, J. and Boudart, M., Springer-Verlag, N.Y., 1981.

Examples of suitable base catalysts include, but are not limited to, metal oxides, hydroxides, carbonates, silicates, phosphates, aluminates and combinations thereof. Preferred are metal oxides, carbonates, and silicates. More preferred are Group 1, Group 2, and rare earth oxides, carbonates, and silicates.

The catalysts of the invention can be used directly as commercially obtained or can be prepared from suitable starting materials using methods known in the art.

The catalysts employed herein may be used in the form of powders, granules, or other particulate forms. Selection of an optimal average particle size for the catalyst will depend upon such process parameters as reactor residence time and desired reactor flow rates.

The catalyst herein may be supported on catalyst support as is common in the art of catalysis. Suitable catalyst supports include, but are not limited to, alumina, titania, silica, zirconia, zeolites, carbon, clays, and combinations thereof. Any method known in the art to prepare the supported catalyst can be used. The support can be neutral, acidic or basic, as long as the surface of the catalyst/support combination is basic. Preferred supports are those which are neutral and have a surface area of greater than about 10 $m^2/g$. Commonly used techniques for treatment of supports with metal catalysts can be found in B. C. Gates, *Heterogeneous Catalysis*, Vol. 2, pp.1–29, Ed. B. L. Shapiro, Tex. A & M University Press, College Station, Tex., 1984.

The catalysts of the present invention may further comprise catalyst additives and promoters that will enhance the efficiency of the catalyst. Use of these materials are common and well known in the art (see for example, *Kirk-Othmer Encyclopedia of Chemical Technology*, Howe-Grant Ed., Vol. 5, pp 326–346, (1993), John Wiley & Sons, New York and *Ullmann's Encyclopedia of Industrial Chemistry*, Vol. A5, Gerhartz et al., Eds., pp. 337–346, (1986), VCH Publishers, New York). The relative percentage of the catalyst promoter may vary as desired. A useful amount of promoter in the process of the invention is from about 0.01% to about 5.00% by weight of catalyst.

A preferred catalyst herein is a metal silicate. By "silicate" is meant an anion consisting of Si, O, and optionally H. These include but are not limited to $SiO_3^{-2}$, $Si_2O_7^{-6}$, and $SiO_4^{-4}$, and their various hydrated forms. More preferred are silicate salts of Group 2 metals of the Periodic Table of Elements; most preferred is magnesium silicate.

One particularly preferred catalyst herein is Magnesol®, a hydrated, synthetic, amorphous form of magnesium silicate produced by The Dallas Group of America, Inc.

Other preferred catalysts are oxides and carbonates of a Group 1, 2, or rare earth metals, optionally supported on a suitable support, and combinations thereof. One method for preparing these catalysts is to dissolve a metal acetate salt in water. A support such as silica is wet with the solution, then calcined. This oxidizes the acetate to the oxide, carbonate, or combination thereof. The more preferred embodiments of the process employ metals from Group 1 or 2 of the Periodic Table. The most preferred embodiment is where the metal catalyst is barium, cesium, or rubidium. Other preferred catalysts include salts of organic acids such as cesium acetate, rubidium acetate, potassium acetate, barium acetate, magnesium acetate, calcium acetate, and mixtures thereof.

A preferred catalyst content range of the supported catalyst is from about 1% to about 30%. A more preferred catalytic metal content range is from about 10% to about 25%. A further preferred catalytic metal content range is from about 12% to about 22%.

The process is preferably performed in the vapor phase. The process can be performed in any suitable reactor such as, but not limited to a pulse, fluidized bed, fixed bed, steady state riser reactor, and a recalculating solids reactor system.

In the present invention, a weight ratio of lactone to alcohol of from about 1/100 to about 100/1 is preferred at the start of the reaction. A weight ratio of about 40/60 to 60/40 at the start of the reaction is further preferred. A weight ratio of about 50/50 is most preferred.

A temperature range of from about 250° C. to about 500° C. is preferred for the processes of the invention. A temperature range of from about 275° C. to about 450° C. is further preferred. A temperature range of from about 325° C. to about 400° C. is most preferred.

A pressure range of from about 1.0 MPa to about 6.9 MPa is employed for the processes of the invention. A pressure range of from about 2.0 MPa to about 4.0 MPa is preferred.

The process of the present invention may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA). The condensate water formed as the product of the reaction is removed by separation methods customarily employed for such separations.

It will be appreciated that the selectivities and yields of product may be enhanced by additional contact with the catalyst. For example, yields and selectivities may be increased where the reactor effluent containing a mixture of reactant and product may be contacted additional times over the catalyst under the reaction conditions set forth herein to enhance the conversion of reactant to product.

The process of the instant invention may additionally comprise the recovery or isolation of one or more of the pentenoate esters. This can be done by any method known in the art, such as distillation, decantation, recrystallization, or extraction.

EXPERIMENTAL

Materials and Methods

The following abbreviations are used herein:

| | |
|---|---|
| Magnesol ® | magnesium silicate (registered trademark of The Dallas Group of America, Inc. |
| VL | gamma-valerolactone or 5-methyl-butyrolactone |
| MP | methyl pentenoate ester |
| M4P | methyl-4-pentenoate ester |
| t-M2P | trans-methyl-2-pentenoate ester |
| t-M3P | trans-methyl-3-pentenoate ester |
| c-M3P | cis-methyl-3-pentenoate ester |
| cc | cubic centimeters |
| Temp. | temperature |
| TOS | time on stream |
| Dist. | distribution |
| Sel. | selectivity |
| Conv. | conversion |

The following procedure is illustrative of the procedure used to prepare base catalysts on silica supports. All metals were used as the acetate salts.

Procedure for Preparation of 20% Cesium on Silica

Cesium acetate (2.91 g; Sigma-Aldrich Corporation St. Louis, Mo.) was dissolved in $H_2O$ (14 ml) and the solution was added dropwise into silica (8.07 g; W. R. Grace, Columbia, Md.; Grade 55, 12×20 mesh). The mixture was allowed to stand at room temperature for 2 hours and then the mixture was transferred into an alumina dish. The dish was placed in a horizontal quartz tube and purged with air. The supported catalyst was heated at 120° C. for 4 hours and then at 450° C. for 16 hours in a stream of air. The sample was then cooled to yield 9.87 g of 20% cesium on silica.

EXAMPLES 1–49

8 cc of catalyst was charged into a ½ inch outer diameter Inconel® (International Nickel Co. of Canada Ltd., Beamsville, Ontario, Canada) tubular reactor heated by a tube furnace. A (weight ratio of 50:50 methanol:VL) aqueous solution of gamma-valerolactone and methanol was pumped into the reactor at a flow rate of 2–6 ml/hr at a rate of 2 cc/hr. The reactor effluent was quenched in a cold solution of methanol (approximately 10° C.). The sample was then analyzed on a HP 5890 gas chromatograph using a flame ionization detector (with a RTX-1701 column 30 m×0.53 mm inner diameter from Restek Co., Bellefonte, Pa.). The detector was held at 50° C. for 3 minutes then heated to 165° C. at a rate of 30° C./min and held for 8 minutes. The selectivity and conversion were then calculated based on normalized area percents. The results are shown in Table 1 below. The table includes the percent VL converted, the percent selectivity to total pentenoate esters, and the distribution of the various pentenoate ester isomers in the total pentenoate esters.

TABLE 1

| Ex. No. | Catalyst | Reaction Temp. (° C.) | TOS (hrs) | % VL Conv. | % MP Sel. | % M4P Dist. | % t-M2P Dist. | % t-M3P Dist. | % c-M3P Dist. |
|---|---|---|---|---|---|---|---|---|---|
| 1. | Magnesol | 300 | 1 | 62.9 | 72.7 | 48.0 | 13.4 | 24.5 | 14.1 |
| 2. | Magnesol | 325 | 0.5 | 64.1 | 76.3 | 43.6 | 15.9 | 25.6 | 14.9 |
| 3. | Magnesol | 325 | 1 | 68.6 | 75.8 | 43.9 | 15.8 | 25.5 | 14.8 |
| 4. | Magnesol | 350 | 1 | 85.5 | 72.8 | 40.4 | 18.7 | 25.7 | 15.3 |
| 5. | Magnesol | 375 | 1 | 97.4 | 64.0 | 39.9 | 21.3 | 24.3 | 14.5 |
| 6. | Magnesol | 400 | 1 | 99.3 | 44.5 | 38.9 | 23.5 | 23.6 | 14.1 |
| 7. | 15% CsOAc/SiO2 | 300 | 1 | 58.5 | 77.3 | 96.0 | 1.7 | 1.4 | 0.9 |
| 8. | 15% CsOAc/SiO2 | 325 | 1 | 62.8 | 93.7 | 93.9 | 2.5 | 2.2 | 1.3 |
| 9. | 15% CsOAc/SiO2 | 350 | 1 | 69.1 | 95.5 | 90.7 | 3.7 | 3.5 | 2.1 |
| 10. | 15% CsOAc/SiO2 | 375 | 1 | 70.3 | 94.0 | 84.0 | 6.3 | 6.1 | 3.6 |
| 11. | 15% CsOAc/SiO2 | 425 | 1.5 | 95.5 | 37.2 | 61.2 | 14.0 | 14.4 | 8.7 |
| 12. | 20% CsOAc/SiO2 | 300 | 1 | 24.8 | 53.6 | 90.5 | 5.0 | 4.5 | 0.0 |
| 13. | 20% CsOAc/SiO2 | 325 | 1 | 27.7 | 51.4 | 73.1 | 8.8 | 10.7 | 7.4 |
| 14. | 20% CsOAc/SiO2 | 350 | 1 | 31.1 | 49.2 | 60.6 | 14.8 | 15.7 | 8.9 |
| 15. | 20% CsOAc/SiO2 | 375 | 1 | 29.5 | 35.8 | 50.6 | 18.1 | 19.8 | 11.5 |
| 16. | 20% CsOAc/SiO2 | 425 | 1 | 42.9 | 19.4 | 44.8 | 19.0 | 21.9 | 13.3 |

TABLE 1-continued

| Ex. No. | Catalyst | Reaction Temp. (° C.) | TOS (hrs) | % VL Conv. | % MP Sel. | % M4P Dist. | % t-M2P Dist. | % t-M3P Dist. | % c-M3P Dist. |
|---|---|---|---|---|---|---|---|---|---|
| 17. | 15% RbOAc/SiO2 | 300 | 1 | 23.4 | 26.4 | 90.4 | 4.7 | 4.9 | 0.0 |
| 18. | 15% RbOAc/SiO2 | 325 | 1 | 26.7 | 29.3 | 72.3 | 10.7 | 10.1 | 7.0 |
| 19. | 15% RbOAc/SiO2 | 350 | 1.5 | 30.5 | 27.4 | 54.4 | 15.1 | 19.1 | 11.4 |
| 20. | 15% RbOAc/SiO2 | 375 | 1 | 29.4 | 28.8 | 50.7 | 17.0 | 20.6 | 11.7 |
| 21. | 15% RbOAc/SiO2 | 425 | 1 | 34.5 | 18.8 | 38.3 | 20.7 | 25.5 | 13.7 |
| 22. | 15% KOAc/SiO2 | 300 | 1 | 49.6 | 14.3 | 100.0 | 0.0 | 0.0 | 0.0 |
| 23. | 15% KOAc/SiO2 | 325 | 1 | 52.9 | 17.4 | 100.0 | 0.0 | 0.0 | 0.0 |
| 24. | 15% KOAc/SiO2 | 350 | 1.5 | 48.2 | 35.9 | 64.6 | 12.9 | 13.5 | 9.0 |
| 25. | 15% KOAc/SiO2 | 375 | 1 | 45.4 | 44.7 | 57.9 | 14.5 | 16.9 | 10.8 |
| 26. | 15% KOAc/SiO2 | 425 | 1 | 44.7 | 34.4 | 43.9 | 18.0 | 23.0 | 14.1 |
| 27. | 15% KOAc/SiO2 | 475 | 1 | 68.0 | 21.1 | 41.9 | 17.5 | 24.5 | 14.5 |
| 28. | 15% NaOAc/SiO2 | 300 | 1 | 40.8 | 55.5 | 92.1 | 3.9 | 4.0 | 0.0 |
| 29. | 15% NaOAc/SiO2 | 325 | 1 | 39.1 | 62.3 | 82.0 | 6.9 | 6.9 | 4.2 |
| 30. | 15% NaOAc/SiO2 | 350 | 1 | 38.8 | 66.5 | 71.6 | 11.0 | 10.8 | 6.6 |
| 31. | 15% NaOAc/SiO2 | 375 | 1 | 44.6 | 64.7 | 65.4 | 12.8 | 13.6 | 8.2 |
| 32. | 15% NaOAc/SiO2 | 425 | 1 | 65.7 | 22.4 | 40.8 | 20.9 | 24.8 | 12.2 |
| 33. | 15% Ba(OAc)2/SiO2 | 300 | 1 | 55.4 | 90.8 | 92.7 | 3.1 | 2.6 | 1.6 |
| 34. | 15% Ba(OAc)2/SiO2 | 325 | 1 | 57.2 | 93.1 | 90.4 | 3.9 | 3.6 | 2.1 |
| 35. | 15% Ba(OAc)2/SiO2 | 350 | 1 | 64.8 | 94.7 | 86.1 | 5.5 | 5.3 | 3.1 |
| 36. | 15% Ba(OAc)2/SiO2 | 375 | 1 | 58.4 | 90.1 | 80.0 | 7.9 | 7.6 | 4.6 |
| 37. | 15% Ba(OAc)2/SiO2 | 425 | 1 | 89.6 | 67.1 | 61.8 | 14.3 | 14.9 | 9.0 |
| 38. | 15% Ba(OAc)2/SiO2 | 325 | 0.5 | 57.9 | 91.6 | 90.7 | 3.8 | 3.4 | 2.1 |
| 39. | 15% Ba(OAc)2/SiO2 | 325 | 6 | 57.0 | 90.9 | 91.1 | 3.5 | 3.3 | 2.0 |
| 40. | 15% Ma(OAc)2-4H20/SiO2 | 300 | 1 | 60.9 | 92.2 | 65.9 | 12.2 | 14.1 | 7.8 |
| 41. | 15% Mg(OAc)2-4H20/SiO2 | 325 | 1 | 63.0 | 89.5 | 60.5 | 14.0 | 16.3 | 9.2 |
| 42. | 15% Mg(OAc)2-4H20/SiO2 | 350 | 1 | 69.1 | 86.1 | 56.8 | 15.3 | 17.6 | 10.3 |
| 43. | 15% Mg(OAc)2-4H20/SiO2 | 375 | 1 | 77.0 | 82.9 | 54.2 | 16.2 | 18.5 | 11.1 |
| 44. | 15% Mg(OAc)2-4H20/SiO2 | 425 | 1 | 96.4 | 49.9 | 48.0 | 19.8 | 20.1 | 12.1 |
| 45. | 15% Ca(Ac)2.H20/SiO2 | 300 | 1 | 55.5 | 89.9 | 89.7 | 3.9 | 4.0 | 2.3 |
| 46. | 15% Ca(Ac)2.H20/SiO2 | 325 | 1 | 61.6 | 92.4 | 88.8 | 4.2 | 4.4 | 2.6 |
| 47. | 15% Ca(Ac)2.H20/SiO2 | 350 | 1 | 61.3 | 92.1 | 86.0 | 5.3 | 5.4 | 3.3 |
| 48. | 15% Ca(Ac)2.H20/SiO2 | 375 | 1 | 68.8 | 90.7 | 83.2 | 6.3 | 6.5 | 4.0 |
| 49. | 15% Ca(Ac)2.H20/SiO2 | 425 | 1 | 85.5 | 62.2 | 75.7 | 9.3 | 9.4 | 5.6 |

What is claimed is:

1. A process for preparing alkyl alkenoate ester represented by Formula III, comprising contacting a lactone of Formula I with an alkanol of Formula II in the presence of a heterogeneous base catalyst, the base catalyst being optionally supported on a catalyst support, to form the corresponding alkyl alkenoate ester,

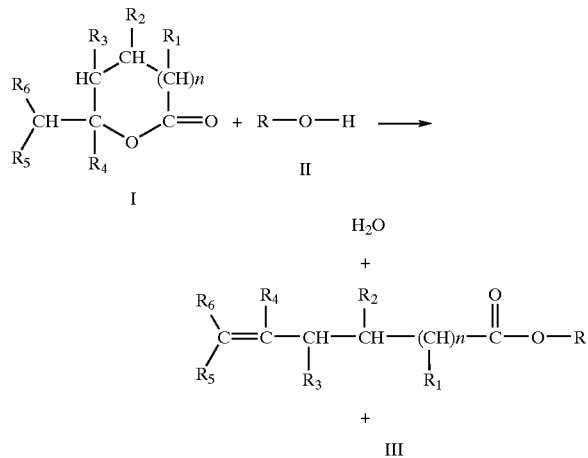

wherein:

n=0–2;

$R_1$, $R_2$, $R_3$, and $R_4$, independently are hydrogen, hydrocarbyl or substituted hydrocarbyl, $C_1$–$C_{18}$ unsubstituted or substituted alkyl, unsubstituted or substituted alkenyl, unsubstituted or substituted cycloalkyl, unsubstituted or substituted cycloalkyl containing at least one heteroatom, unsubstituted or substituted aryl, and unsubstituted or substituted heteroaryl;

$R_5$ and $R_6$ taken independently are hydrogen or alkyl with 1 to 5 carbon atoms, wherein the total number of carbons of $R_5$ and $R_6$ do not exceed 5; and R is alkyl with 1 to 6 carbon atoms.

2. The process as recited in claim 1 wherein n=0 and R1, R2, R3, R4, R5, and R6, taken independently, are hydrogen.

3. The process as recited in claim 2 wherein R is a methyl group.

4. The process as recited in claim 1 wherein the lactone is gamma-valerolactone and the alkanol is methanol.

5. The process as recited in claim 1 or claim 4 wherein the ratio of weight content of the lactone to the alkanol is in the range of from 1/100 to 100/1.

6. The process as recited in claim 1 or claim 4 wherein the ratio of weight content of the lactone to the alkanol is in range of from 40/60 to 60/40.

7. The process as recited in claim 1 wherein the base catalyst is selected from the group consisting of metal silicates, metal carbonates, metal oxides, metal hydroxides, metal phosphates, metal aluminates or combinations thereof.

8. A process as recited in claim 1 wherein the base catalyst is selected from the group consisting of Group 1, Group 2 or rare earth silicates; Group 1, Group 2 or rare earth oxides; Group 1, Group 2 or rare earth carbonates; and combinations thereof.

9. The process as recited in claim 1 wherein the process is performed at a temperature in the range of from 250° C. to 500° C.

10. The process as recited in claim 1 wherein the process is performed at a temperature in the range of from 325° C. to 400° C.

11. The process as recited in claim 6 wherein said metal is selected from the group consisting of barium, cesium, rubidium and magnesium.

12. The process as recited in claim 7 wherein the base catalyst content is of from about 1% to about 30% by weight of the reactants.

13. The process as recited in claim 7 wherein the base catalyst content is of from about 10% to about 25% by weight of the reactants.

14. The process as recited in claim 7 wherein the base catalyst content is of from about 12% to about 22% by weight of the reactants.

15. The process as recited in claim 1 wherein the process is performed in a vapor phase.

* * * * *